United States Patent [19]
Ojima

[11] Patent Number: 5,294,737
[45] Date of Patent: Mar. 15, 1994

[54] PROCESS FOR THE PRODUCTION OF CHIRAL HYDROXY-β-LACTAMS AND HYDROXYAMINO ACIDS DERIVED THEREFROM

[75] Inventor: Iwao Ojima, Stony Brook, N.Y.

[73] Assignee: The Research Foundation State University of New York, Albany, N.Y.

[21] Appl. No.: 842,444

[22] Filed: Feb. 27, 1992

[51] Int. Cl.$^5$ ............................................ C07C 229/00
[52] U.S. Cl. .................................................... 562/444
[58] Field of Search ........................................ 562/444

[56] References Cited

U.S. PATENT DOCUMENTS

| | | | |
|---|---|---|---|
| 4,352,752 | 10/1982 | Ojima et al. | 562/444 |
| 4,562,263 | 12/1985 | Ohashi et al. | |
| 4,814,470 | 3/1989 | Colin et al. | |
| 4,814,485 | 3/1989 | Descamps et al. | 562/444 |
| 4,857,653 | 8/1989 | Colin et al. | |
| 4,876,399 | 10/1989 | Holton et al. | |
| 4,898,977 | 2/1990 | Herold et al. | 562/444 |
| 4,924,011 | 5/1990 | Denis et al. | |
| 4,924,012 | 5/1990 | Colin et al. | |
| 4,960,790 | 10/1990 | Stella et al. | |
| 4,992,544 | 2/1991 | Miller | 540/355 |
| 5,015,744 | 5/1991 | Holton . | |

FOREIGN PATENT DOCUMENTS 3743225 6/1989 Fed. Rep. of Germany ...... 562/444

OTHER PUBLICATIONS

Ojima et al, "Efficient and practical asymmetric synthesis of the taxol . . ." J. Org. Chem. 56(5), 1681–3, 1991, CA 114(13):122752q. Chemical Abstracts citation only.
I. Ojima et al., Tetrahedron Letter (1990), 31, 4289–4292.
J. N. Denis et al., J. Org. Chem. (1990), 55, 1957–1959.
D. J. Hart et al., Chem. Rev. (1989), 89, 1447–1465.
J. N. Denis et al., J. Org. Chem. (1986), 51, 46–50.
D. J. Hart et al., J. Am. Chem. Soc. (1986), 108, 6054–6056.

*Primary Examiner*—Jose G. Dees
*Assistant Examiner*—Keith MacMillan

[57] ABSTRACT

The reaction between a hydroxyacetic acid derivative bearing an oxygen protecting group and a chiral auxiliary group and an imine produces chiral β-lactams. Hydrolysis of the chiral β-lactams produces chiral amino acid analogs.

15 Claims, No Drawings

PROCESS FOR THE PRODUCTION OF CHIRAL HYDROXY-β-LACTAMS AND HYDROXYAMINO ACIDS DERIVED THEREFROM

This work was partially supported by grants from the National Institutes of Health (GM33665 and GM42798).

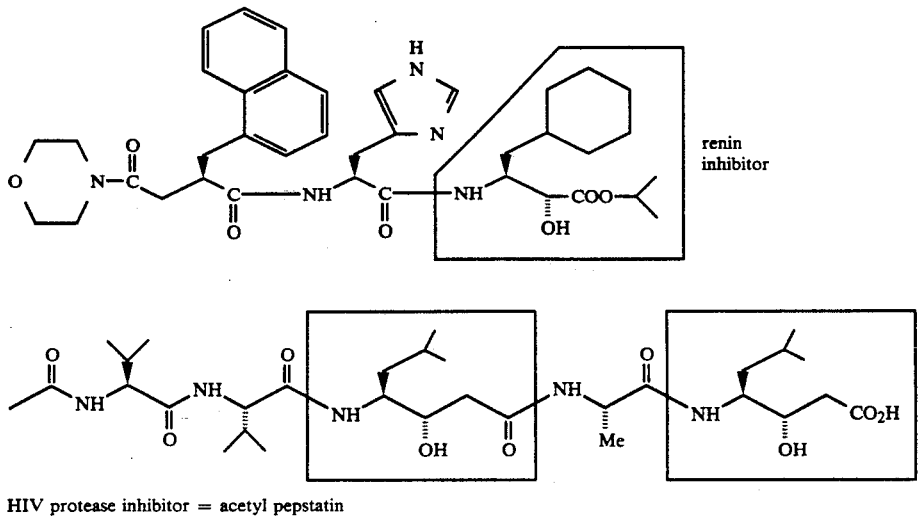

renin inhibitor

HIV protease inhibitor = acetyl pepstatin

BACKGROUND OF THE INVENTION

1. Field of The Invention

The invention relates to the synthesis of hydroxy-β-lactams with high enantiomeric purity and hydroxyamino acids derived therefrom.

The development of a process for the efficient production of hydroxy-β-lactams and their derivatives with high enantiomeric purity in high yield is of great importance for the synthesis of biologically active compounds of medicinal interest. The hydroxy-β-lactams with high enantiomeric purity can serve as precursors for the production of 2-hydroxy-3-amino acids (isoserines).

2. Background of Related Art

The hydroxyamino acids are an important class of amino acids, which include norstatine, statine, and their analogs. The structures of norstatine and statine are as follows:

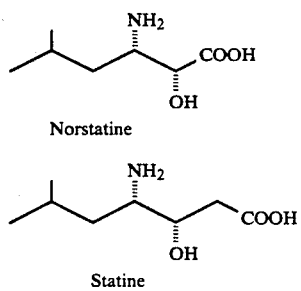

Norstatine

Statine

These amino acids and their derivatives serve as important components of enzyme inhibitors for a variety of peptide-degrading enzymes (peptidases). Furthermore, hydroxy-β-lactam with high enantiomeric purity can serve as a key intermediate in the semisynthesis of the important anti-tumor chemotherapeutic agent, taxol.

Norstatine, statine and their analogs have been used extensively as crucial amino acid residues in peptide-based inhibitors of such enzymes as renin and HIV protease. Structures of typical enzyme inhibitors of renin and HIV protease are shown below:

Renin inhibitors are very specific antihypertensive agents, and HIV protease inhibitors are expected to serve as key therapeutic agents for AIDS. Norstatine, statine and their analogs provide effective transition state mimics of the substrates for peptidases, which bind to the enzymes tightly and inhibit their actions. Those enzyme inhibitions are very sensitive to the enantiomeric purity of the hydroxyamino acid residues.

Taxol is a complex diterpene isolated from the bark of *Taxus brevifolia* (Pacific Yew). The structure of taxol is as follows:

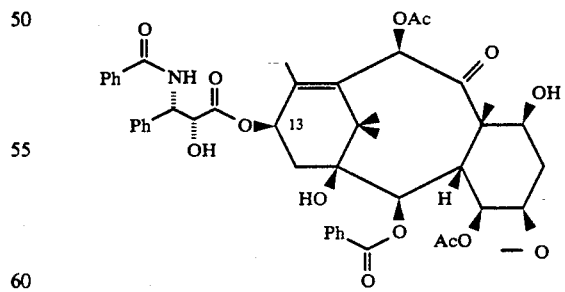

Taxol possesses high cytotoxicity and strong antitumor activity and is currently in phase III clinical trials in the United States.

A more readily available taxol precursor can be isolated from the leaves of *Taxus baccata*. Extraction of fresh leaves yields 10-deacetyl baccatin III which has the following structure:

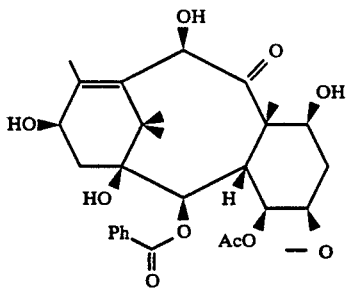

With the availability of 10-deacetyl baccatin III, taxol can be produced in a semi-synthetic fashion with the coupling of a side chain which is a N-benzoyl-(2R,3S)-3-phenylisoserine having the following structure:

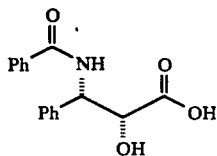

Synthesis of the side chain via a Sharpless epoxidation in a process requiring eight steps has been described by Denis, J. N., et al., "An Efficient, Enantioselective Synthesis of the Taxol Side Chain", J. Org. Chem. 51, 46–50 (1986). The Denis et al. mode of synthesis of the taxol side chain is as follows:

Phenylacetylene is subject to 1) hydroxymethylation followed by 2) Lindlar reduction to yield cis-cinnamyl alcohol.

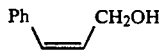

3) The cis-cinnamyl alcohol is subjected to the titanium-catalyzed epoxidation process to yield (2S,3R)-epoxy alcohol.

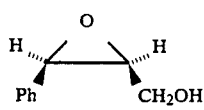

4) This epoxy alcohol is oxidized with RuCl$_3$ and NaIO$_4$, and 5) the reaction product converted to the methyl ester of the epoxide with ethereal diazomethane. 6) This methyl ester of the epoxide is transformed into the desired hydroxyazide by epoxide cleavage using azidotrimethylsilane and a catalytic amount of zinc chloride followed by acid hydrolysis.

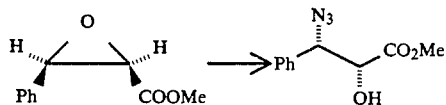

7) The hydroxy azide is transformed into azido benzoate and hydrogenated in methanol to produce amino benzoate. 8) The amino benzoate is rearranged to give the product.

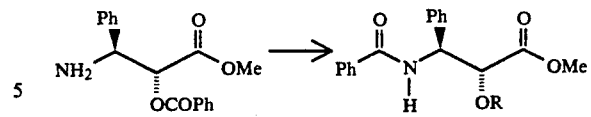

Modifications in this method have also been described by Denis, J. N. et al., "An Improved Synthesis of the Taxol Side Chain and of RP56976", J. Org. Chem 55, 1957–1959 (1990).

U.S. Pat. No. 5,015,744 to Holton describes another process for preparing the side chain of taxol. In the Holton process, the starting materials are acyloxyacetyl chloride cyclocondensed with an imine derived from benzaldehyde and p-methoxyaniline. The reaction produces racemic hydroxy-$\beta$-lactams which must be resolved into the pure enantiomers. After the optical resolution, the (3R,4S)-hydroxy-$\beta$-lactam is reacted with ethyl vinyl ether and then converted to an oxazinone:

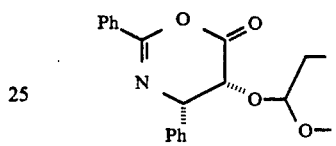

The oxazinone is reacted with 7-O-triethylsilyl baccatin III to form the last precursor to taxol.

For antitumor activity of taxol, the side chain, N-benzoyl-(2R,3S)-3-phenylisoserine is crucial. This side chain must be highly enantiomerically pure.

Accordingly, it is an object of the invention to synthesize hydroxy-$\beta$-lactams in high yield with high enantioselectivity, with a minimum of synthesis steps.

It is a further object of the invention to provide hydroxy-$\beta$-lactams which act as precursors for a variety of biologically active compounds such as the side chain of taxol and its analogs and also norstatine, statine, their analogs, and other amino acid residues.

SUMMARY OF THE INVENTION

A process is provided for the production of chiral hydroxy-$\beta$-lactams of the formula

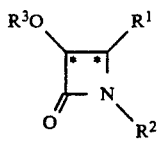

wherein
$R^1$ is as defined below in an imine;
$R^2$ is hydrogen, or a $R^7$ group of an imine as defined below;
$R^3$ is hydrogen or an oxygen protecting group $R^4$.

The process comprises first generating an enolate by reacting an oxygen-protected hydroxyacetic acid derivative of the formula $$R^4OCH_2C(O)Xc$$

wherein
$R^4$ is an oxygen protecting group, and
Xc is a chiral auxiliary group, with a base of the formula

MNR⁵R⁶ wherein

M is an alkali metal, and

—NR⁵R⁶ is a disubstituted amino group of 1 to 20 carbons or —NR⁵R⁶ is a bis(trialkylsilyl)amino group of 1 to 20 carbons, followed by cyclocondensing the ester enolate with an imine having the formula

wherein

R¹ is a branched or straight chain alkyl, cycloalkyl, alkenyl, alkynyl, aryl, or substituted aryl, aryl also including heteroaromatic, and R¹ includes 1 to 20 carbons;

R⁷ is a branched or straight chain alkyl, cycloalkyl, alkenyl, alkynyl, aryl, substituted aryl, heteroaromatic or substituted heteroaromatic, and R⁷ includes 1 to 20 carbons, or R⁷ is a trisubstituted silyl of 3 to 20 carbons, to yield the chiral β-lactams. The chiral β-lactams may be deprotected and hydrolyzed to yield the corresponding chiral hydroxyamino acids.

In one embodiment, the phenylisoserine side chain of taxol with high enantiomeric purity may be produced by reacting an O-protected hydroxyacetate of the formula R⁴OCH₂C(O)Xc wherein R⁴ is triisopropylsilyl, Xc is (—)-trans-2-phenyl-1-cyclohexyloxy, with lithium diisopropylamide followed by cyclocondensing with an imine of the formula

wherein

R¹ is phenyl and R⁷ is trimethylsilyl, to form a chiral oxygen-protected hydroxy-β-lactam of the formula

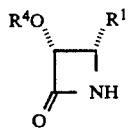

wherein

R¹ and R⁴ are as defined immediately above, hydrolyzing the oxygen-protected hydroxy-β-lactam with hydrochloric acid to yield a hydrochloric acid salt of (2R,3S)-phenylisoserine having the formula

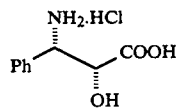

and benzoylating the phenylisoserine.

In another embodiment, norstatine or its cyclohexyl analog of the formula

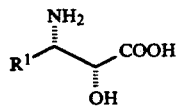

may be produced by reacting an oxygen-protected hydroxyacetic acid derivative of the formula R⁴OCH₂C(O)Xc wherein R⁴ is triisopropylsilyl, Xc is (—)-trans-2-phenyl-1-cyclohexyloxy, with lithium diisopropylamide, followed by cyclocondensing with an imine of the formula

wherein R¹ is isobutyl or cyclohexylmethyl, R⁷ is p-methoxyphenyl to give a β-lactam of the formula

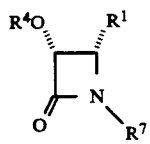

wherein R¹, R⁴, and R⁷ are defined immediately above, deprotecting the β-lactam nitrogen with cerium ammonium nitrate and hydrolyzing the resulting β-lactam with hydrochloric acid to give norstatine or (2R,3S)-3-amino-4-cyclohexyl-2-hydroxybutanoic acid as hydrochloric acid salt.

Advantageously, the chiral ester enolate-imine cyclocondensation method of the invention allows high yields and high enantioselectivity in a minimum of reaction steps.

For a better understanding of the present invention, together with other and further objects, reference is made to the following description and its scope will be pointed out in the appended claims.

DETAILED DESCRIPTION OF THE INVENTION

A chiral enolate-imine cyclocondensation strategy can be used in the asymmetric synthesis of chiral β-lactams. Using this method, 2-hydroxy-3-amino acids, i.e., isoserines, including norstatine and its analogs as well as the C-13 side chain of taxol and its analogs can be obtained with the use of chiral β-lactams as key intermediates. The chiral β-lactam synthesis can be carried out with only two steps in one-pot. High enantiomeric purity of the product is achieved through the use of a chiral auxiliary in the starting hydroxyacetic acid derivative.

The cyclocondensation strategy is used to synthesize non-protein amino acids with high enantiomeric purity and dipeptides containing those non-protein amino acid residues which are potential enzyme inhibitors, fragments of peptide hormone analogues and components of naturally occurring glycosphingolipids and antibiotics. Examples of products with economic importance are enantiometrically pure norstatine and its analogs, which are the crucial components of enzyme inhibitors for renin and HIV protease, and the side chain of taxol, a potent anticancer therapeutic agent.

In the synthesis process, a hydroxyacetic acid derivative with a protected hydroxyl and a chiral auxiliary group is first reacted with a base to generate a chiral enolate in situ. The enolate is reacted with an imine to yield the corresponding chiral β-lactams. The chiral β-lactam may be hydrolyzed to yield a 2-hydroxy-3-amino acid (an isoserine) with high enantiometric purity.

Chiral β-lactams may be synthesized according to the following reaction Scheme 1:

verted to the corresponding chiral non-racemic, i.e., optically active, product.

In the method of current invention, the chiral auxiliary is detached during the reaction and easily recovered so that it is recyclable. This is one of the advantageous aspects of the method of this invention. The chiral auxiliary moiety used in this method of invention arises from the corresponding chiral alcohol or oxazolidinone, i.e., Xc—H is either a chiral alcohol or oxazolidinone.

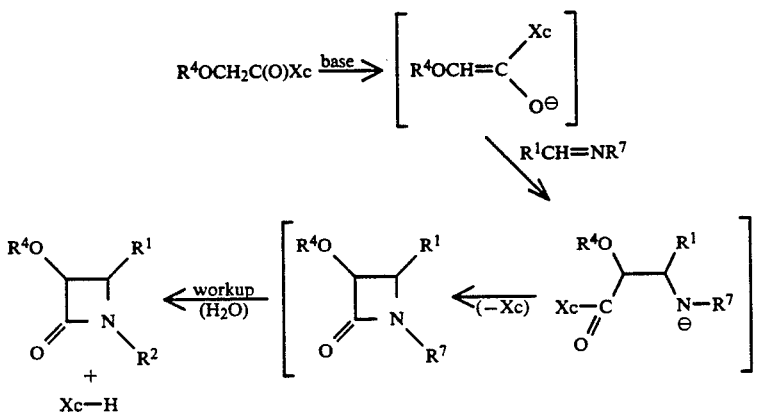

Scheme 1

Steps (including workup) of the reaction may be carried out in a preferred temperature range of from about −100° C. to about 40° C., more preferably at about −85° C. to about 25° C., and in an organic solvent such as dry non-protic organic solvent such as tetrahydrofuran, dioxane, ether, monoglyme, diglyme, dimethylformamide, mixtures of those solvents with hexane, toluene, and xylene. The method is preferably carried out under inert gas atmosphere such as nitrogen and argon. The amount of a base such as lithium diisopropylamide, lithium hexamethyl-disilazide, sodium diisopropylamide, potassium diisopropylamide, and lithium dicyclohexylamide, utilized for the reaction is preferably approximately equivalent to the amount of chiral O-protected hydroxyacetic acid or its derivative, but the use of a slight excess of the base does not adversely affect the reaction. For purposes of economy and efficiency, the ratio of hydroxyacetatic acid derivative: base: imine reactants utilized in the reaction is preferably approximately equivalent, but the ratio is not critical.

Work-up means any routine isolation procedure to obtain the product from the reaction mixture.

The hydroxyacetic acid derivative is represented by formula 1:

$$R^4OCH_2C(O)Xc \qquad 1$$

wherein $R^4$ represents an oxygen protecting group, and

Xc represents an enantiomerically pure group which will be called a chiral auxiliary moiety.

The term chiral auxiliary, as used in the field of synthetic organic chemistry or more specifically in the field of asymmetric synthesis, is intended to mean a chiral non-racemic moiety that is attached to a prochiral substrate prior to the reaction, directing the asymmetric organic reaction by transferring its chirality to the reaction site, which is eventually detached from the reaction product so that overall the prochiral substrate is con- Representative chiral auxiliaries for Xc—H include (−)-menthol, (+)-neomenthol, (−)-borneol, isopinocampheneol, (+)- and (−)-trans-2-phenyl-1-cyclohexanol, (−)-10-dicyclohexylsulfamoyl-D-isoborneol, (−)-8-phenylmenthol, (+)-cinchonine, (−)-cinchonidine, quinine, quinidine, N-methylephedrine, (+)- and (−)-4-isopropyloxazolylidin-2-one, and (+)- and (−)-4-phenyloxazolidin-2-one. Preferred chiral auxiliaries for Xc—H are (+)- and (−)-trans-2-phenyl-1-cyclo-hexanol.

The oxygen protecting group $R^4$ may be represented by formula 2 or formula 3. Formula 2 is as follows:

$$R^8R^9R^{10}Y- \qquad 2$$

wherein

Y is carbon, silicon, germanium, or tin, preferably silicon;

$R^8$, $R^9$ and $R^{10}$ independently represent branched or straight chain alkyl, cycloalkyl, alkenyl, alkynyl, aryl, substituted aryl, alkoxy, aryloxy, heteroaromatic, subtituted heteroaromatic, trialkylsilyl or trialkylsiloxy; $R^8$, $R^9$ and $R^{10}$ can be connected with each other to form a cyclic structure. Heteroaromatic groups may also include atoms of oxygen, nitrogen, and sulfur. $R^8$, $R^9$ and $R^{10}$ each include 1 to 15 carbons.

Examples for $R^8$, $R^9$ and $R^{10}$ include methyl, ethyl, propyl, isopropyl, butyl, isobutyl, sec-butyl, tert-butyl, pentyl, isopentyl, neopentyl, hexyl, isohexyl, thexyl, cyclohexyl, phenyl, tolyl, xylyl, biphenyl, naphthyl, trimethylsilyl, triethylsilyl, dimethylphenyl, diphenylmethyl, trimethoxysilyl, triethoxylsilyl, methyldimethoxylsilyl, dimethylmethoxylsilyl, methoxy, ethoxy, propoxy, isopropoxy, butoxy, isobutoxy, sec-butoxy, tert-butoxy, pentoxy, isopentoxy, neopentoxy, hexyloxy, isohexyloxy, thexyloxy, cyclohexyloxy, phenoxy, tolyloxy, xylyloxy, biphneyloxy, naphthyloxy, trimethylsilyloxy, triethylsilyloxy, dimethylphenylsilyloxy, diphenylmethylsilyloxy, trimethoxysilyloxy, triethoxylsilyloxy, methyldimethoxylsilyloxy, dimethylmethoxysilyloxy.

Preferred oxygen protecting groups for formula 2 are triisopropylsilyl, tert-butyldimethylsilyl, tert-butyldiphenylsilyl, triethylsilyl, di-tert-butylmethylsilyl, di-tert-butylphenylsilyl, dimethylthexylsilyl, triisobutylsilyl, dicyclohexylmethylsilyl, cyclohexyldimethylsilyl and triphenylmethyl (trityl).

Formula 3 for the oxygen protecting group $R^4$ is as follows:

$$R^{11}R^{12}Z—$$

wherein

Z is boron or aluminum, and $R^{11}$ and $R^{12}$ independently represent branched or straight chain alkoxy, cycloalkyloxy, aryloxy, substituted aryloxy, heteroaromatic, substituted heteroaromatic, trialkylsilyl or trialkylsiloxy. $R^{11}$ and $R^{12}$ can be connected to each other to form a cyclic structure. $R^{11}$ and $R^{12}$ each include 1 to 15 carbons.

Examples for $R^{11}$ and $R^{12}$ include methoxy, ethoxyl, isopropoxy, isobutoxy, neopentyloxy, cyclohexyloxy, phenoxy, 2,4,6-trimethylphenoxy, 2,4,6-triisopropylphenoxy, 2,6-di-tert-butyl-4-methyphenoxy. Preferred oxygen protecting groups for formula 3 include bis(2,4,6-trimethyl-phenoxy)alanyl, bis(2,4,6-triisopropylphenoxy)alanyl, bis(2,6-di-tert-butyl-4-methyphenoxy)alanyl and 9-borabicyclo[3.3.1]nonan-9-yl.

Representative oxygen protecting groups for $R^4$ are triisopropylsilyl, t-butyldimethylsilyl, tert-butyldiphenylsilyl, trimethylsilyl, triethylsilyl, tripropylsilyl, tributylsilyl, trihexylsilyl, trioctylsilyl, di-tert-butylmethylsilyl, di-tert-butylphenylsilyl, dimethylthexylsilyl, triisobutylsilyl, dicyclohexylmethylsilyl, cyclohexyldimethylsilyl, diisopropyloctylsilyl, diisobutyloctylsilyl, triphenylsilyl, and triphenylmethyl (trityl).

The $R^4$ oxygen protecting groups can easily removed from the β-lactam products by a simple manipulation such as treating with fluoride ion to afford the corresponding 3-hydroxy-β-lactams.

The hydroxyacetic acid derivative represented by $R^4OCH_2C(O)Xc$ is reacted with a base represented by formula 4 to generate the corresponding enolate. Formula 4 for the base is as follows:

$$MNR^5R^6 \qquad 4$$

wherein

M is alkali metal including lithium, sodium, potassium, or cesium;

$R^5$ and $R^6$ independently represent branched or straight chain alkyl, cycloalkyl, and trialkylsilyl, and $R^5$ and $R^6$ each include 1 to 10 carbons.

Examples for $R^5$ and $R^6$ include methyl, ethyl, propyl, isopropyl, butyl, isobutyl, hexyl, cyclohexyl, octyl, and trimethylsilyl.

Representative bases for formula 4 are lithium diisopropylamide, lithium diethylamide, lithium dicyclohexylamide, lithium ethylcyclohexylamide, lithium hexamethylsilazide, sodium diisopropylamide, sodium hexamethyldisilazide, potassium diisoporylamide, and potassium hexamethylsilazide. Preferred bases are lithium diisopropylamide, lithium ethylcyclohexylamide, lithium dicyclohexylamide, and lithium hexamethyldisilazide.

The enolate thus generated by the reaction of the hydroxyacetic acid derivative (formula 1) and the base (formula 4), is reacted with an imine having the formula 5:

$$R^1CH=NR^7 \qquad 5$$

wherein $R^1$ represents $C_{1-20}$ branched or straight chain alkyl, alkenyl, alkynyl, aryl, substituted aryl, heteroaromatic or substituted heteroaromatic. Heteroaromatic groups may include atoms of nitrogen, oxygen and sulfur.

Examples for $R^1$ include methyl, ethyl, propyl, isopropyl, butyl, isobutyl, tert-butyl, pentyl, neopentyl, hexyl, cyclohexyl, octyl, decyl, ethenyl, crotyl, allyl, butenyl, hexenyl, octenyl, decenyl, 2-phenylethenyl, 2-furanylethenyl, 2-thienylethenyl, 2-pyrrolylethenyl, 2-pyridinylethenyl, 2-(N-acetylindenyl)ethenyl, propargyl, trimethylsilylpropargyl, butynyl, hexynyl, octynyl decynyl, phenyl, tolyl, xylyl, biphenyl, p-methoxyphenyl, 3,4-dimethoxyphenyl, p-acetoxyphenyl, 3,4-diacetoxyphenyl, 4-acetoxy-3-methoxylphenyl, and 3,4-methylenedioxyphenyl.

$R^7$ represents trisubstituted silyl of $C_3$-$C_{20}$, or a straight chain or branched alkyl, cycloalkyl, alkenyl, aryl, substituted aryl, heteroaromatic or substituted heteroaromatic, and $R^7$ includes 1 to 20 carbon atoms. Heteroaromatic groups may include atoms of nitrogen, oxygen, and sulfur. Examples for $R^7$ include trimethylsilyl, triethylsilyl, tert-butyldimethylsilyl, dimethylphenylsilyl, methyl, ethyl, propyl, isopropyl, butyl, isobutyl, tert-butyl, hexyl, octyl, benzyl, 4-methoxybenzyl, 4-nitrobenzyl, allyl, crotyl, phenyl, tolyl, xylyl, naphthyl, biphenyl, and 4-methoxyphenyl.

When $R^7$ is trisubstituted silyl, $R^7$ is converted to hydrogen during the workup (see Scheme 1).

When the desired product is the side chain of taxol, N-benzoyl-(2R,3S)-3-phenylisoserine, $R^1$ is phenyl, and $R^7$ is preferably trimethylsilyl. In this synthesis the product of the reaction Scheme 1 is (3R,4S)-3-triisopropylsilyloxy-4-phenyl-2-azetidin-2-one (see Scheme 2), which is hydrolyzed, for example with hydrochloric acid, to yield the corresponding (2R,3S)-3-phenylisoserine as hydrochloric acid salt. The phenylisoserine is then benzoylated by procedures known in the art, for example, the Schotten-Baumann procedure, and purified, if necessary, by recrystallization or through a short silica gel column to give enantiomerically pure N-benzoyl-(2R,3S)-3-phenylisoserine (see Scheme 3).

The β-lactam obtained in this process can also readily be transformed to (3R,4S)-1-benzoyl-3-(ethoxyethyl)-4-phenylazetidin-2-one (see Scheme 3), a key compound for the coupling with 7-triethylsilylbaccatin III in the taxol semisynthesis process. An example of a coupling process is described in U.S. Pat. No. 5,015,744 to Holton.

Representative reactions for the production of N-benzoyl-(2R,3S)-3-phenylisoserine as well as 1-benzoyl-3-(ethoxy)ethoxy-4-phenylazetidin-2-one are summarized in schemes 2 and 3:

Scheme 2

$$^iPr_3SiOCH_2C(O)Xc \xrightarrow[\text{3. }H_2O]{\text{1. LDA} \\ \text{2. PhCH=NSiMe}_3} \quad \begin{array}{c} ^iPr_3SiO \quad Ph \\ \diagup \\ \square - NH \\ \diagup \\ O \end{array}$$

LDA = $LiN(Pr^i)_2$

Scheme 3

Xc = (—)-trans-2-phenyl-1-cylohexyloxy

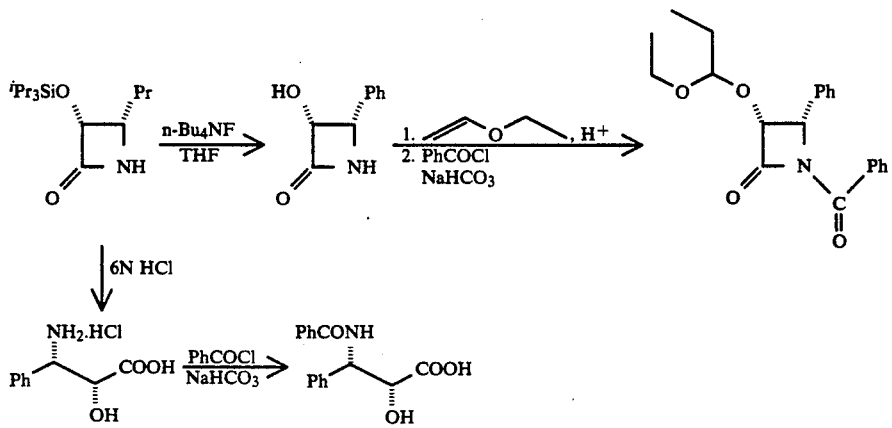

The choice for chiral auxiliary (Xc—H) and oxygen protecting group ($R^1$) exerts an effect on the enantioselectivity as well as the chemical yield of the reaction. One of the preferred combinations is (—)-trans-2-phenyl-1-cyclohexanol as the chiral auxiliary and triisopropylsilyl as the oxygen protecting group.

Depending on the choices for the $R^1$ substituents, the method of this invention can also be used in the asymmetric synthesis of 3-hydroxy-4-substituted-$\beta$-lactams which yield norstatin and its analogs upon deprotection and hydrolysis. In these syntheses, $R^4$ is, for example, triisopropylsilyl, Xc is, for example, (—)-trans-2-phenyl-1-cyclohexyl, $R^1$ is isobutyl, cyclohexylmethyl, furanyl, 2-phenylethenyl, or 2-furanylethenyl, and $R^7$ is 4-methoxyphenyl.

For the synthesis of norstatine and its analogs, the chiral enolate-imine cyclocondensations may be carried out, for example, by reacting (—)-trans-2-phenyl-1-cyclohexyl triisopropylsilyloxyacetate with lithium diisopropylamide (LDA) to generate the corresponding chiral enolate, followed by the addition of N-4-methoxyphenylimine in tetrahydrofuran (THF) to give the corresponding (3R,4S)-1-(4-methoxyphenyl)-3-triisopropylsilyloxy-4-substituted-azetidin-2-ones in high yields as illustrated in Scheme 4.

The removal of the 4-methoxyphenyl group by treatment with cerium ammonium nitrate (CAN) in THF, followed by hydrolysis with hydrochloric acid may be carried out to give the corresponding (2R,3S)-3-substituted isoserines in high yields (see Scheme 4).

Scheme 4

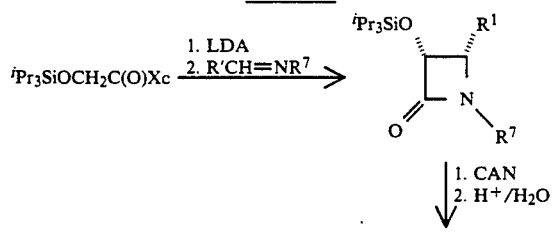

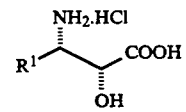

Xc = (—)-2-trans-2-phenyl-1-cyclohexyl
$R^7$ = 4-methoxyphenyl

The furanyl, 2-phenylethenyl, and 2-furanylethenyl groups in these $\beta$-lactams or isoserines can be easily manipulated for further functional group transformations. For example, a $\beta$-lactam bearing 2-phenylethenyl at 4-position is converted to the corresponding 4-(2-phenylethyl)-$\beta$-lactam and 4-(2-cyclohexylethyl)-$\beta$-lactam in high yield. These $\beta$-lactams are hydrolyzed with hydrochloric acid to yield (2R,3S)-3-amino-2-hydroxy-5-phenylpentanoic acid hydrochloride and (2R,3S)-3-amino-2-hydroxy-5-cyclohexylpentanoic acid hydrochloride as illustrated in Scheme 5.

Scheme 5

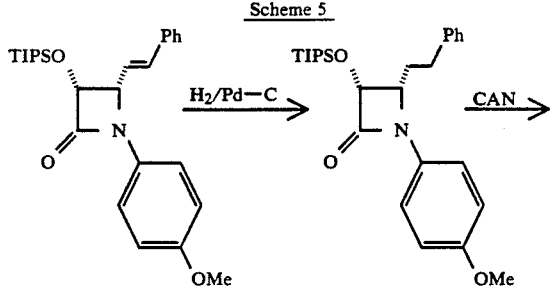

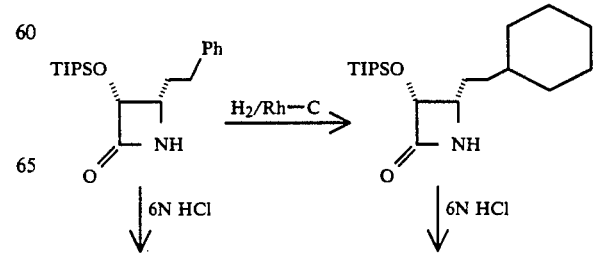

-continued
Scheme 5

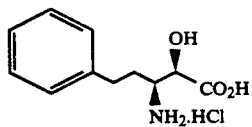 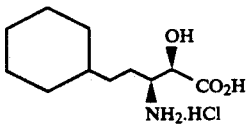

TIPS = triisopropylsilyl

The following non-limiting examples illustrate the invention.

EXAMPLES 1-6

Chiral lithium ester enolates were generated in situ from silyloxyacetates in the presence of lithium diisopropylamide (LDA) with N-trimethylsilylimines to give the corresponding chiral β-lactams as shown in Schemes 1 and 3.

The silyloxyacetate starting materials were employed as follows:

(1a) (−)-Menthyl t-butyldimenthylsilyloxyacetate (t—BuMe$_2$Si—OCH$_2$COO—(−)-menthyl)

(1b) (1R,2S)-2-Phenyl-1-cyclohexyl-t-butyldimethyl-silyloxyacetate (t—BuMe$_2$Si—OCH$_2$COO—(−)-trans-2-phenyl-1-cyclohexyl)

(1c(−)) (1R,2S)-2-phenyl-1-cyclohexyl triisopropyl-silyl-oxyacetate (i—Pr$_3$Si—OCH$_2$COO—(−)-trans-2-phenyl-1-cyclohexyl)

(1c(+)) (1R,2S)-2-phenyl-1-cyclohexyl triisopropyl-silyl-oxyacetate (i—Pr$_3$Si—OCH$_2$COO—(+)-trans-2-phenyl-1-cyclohexyl)

To obtain 1c(−), a solution of (−)-(1R,2S)-2-phenyl-1-cyclohexyl hydroxyacetate (851 mg, 3.63 mmol) was prepared through esterification of benzyloxyacetyl chloride with (−)-(1R,2S)-2-phenyl-1-cyclohexanol followed by hydrogenolysis. Then, triisopropylsilyl chloride (840 mg, 4.36 mmol) and imidazole (618 mg, 9.08 mmol) in dimethylformamide (DMF) (1.7 mL) was stirred at room temperature for 12–20 hours. The mixture was poured into pentane (25 mL), and washed with water and brine. The combined organic layers were dried over anhydrous MgSO$_4$ and concentrated in vacuo. The crude product was subjected to a purification on a short silica gel column using hexane/chloroform (3/1) as the eluant to give pure 1c(−) (1.35 g, 95% yield) as a colorless oil.

In the same manner, 1a, 1b, and 1c(+) were prepared from the combinations of (−)-menthyl hydroxyacetate with tertbutyldimethylsilyl chloride, (−)-(1R,2S)-2-phenyl-1-cyclohexyl hydroxyacetate with tert-butyldimethylsilyl chloride, and (+)-(1S,2R)-2-phenyl-1-cyclohexyl hydroxyacetate with triisopropylsilyl chloride, respectively, in 90–95% yields.

Identification data for the chiral silyloxyacetates (1) are shown below:

1a: Colorless oil; $[\alpha]_D^{20}$−59.3° (c 1.00, CHCl$_3$); 1H NMR (CDCl$_3$) δ 0.11 (s, 6H), 0.76 (d, J=7.0 Hz, 3H), 0.88 (d, J=6.9 Hz, 3H), 0.90 (d, J=6.4 Hz, 3H), 0.92 (s,9H), 0.90–1.13 (m, 3H), 1.32–1.43 (m, 1H), 1.40–1.56 (m, 1H), 1.63–1.72 (m, 2H), 1.80–1.91 (m, 1H), 1.98–2.05 (m, 1H), 4.22 (s, 2H), 4.75 (ddd, J=10.9, 10.9, 4.4 Hz, 1H). HRMS Calcd for C$_{18}$H$_{36}$O$_3$Si: C, 65.80; H, 11.05. Found: C, 65.60; H, 10.96.

1b: Colorless oil; $[\alpha]_D^{20}$−18.7° (c 1.03, CHCl$_3$); 1H NMR (CDCl$_3$) δ −0.08 (s,3H),., −0.06 (s, 3H), 0.83 (s, 9H), 1.25–1.62 (m, 4H), 1.76–1.98 (m, 3H), 2.10–2.17 (m, 1H), 2.66 (dt, J=3.7, 11.5 Hz, 1H), 3.83 (d, J=16.8 Hz, 1H), 3.99 (d, J=16.8 Hz, 1H), 5.06 (dt, J=4.4, 10.5 Hz, 1H), 7.18–7.31 (m, 5H). Anal. Calcd for C$_{20}$H$_{32}$O$_3$Si: C, 68.92; H, 9.25. Found: C, 68.83; H, 9.18.

1c(−): Colorless oil; $[\alpha]_D^{20}$−17.1° (c 3.15, CHCl$_3$; 1H NMR (CDCl$_3$) δ 0.93–0.99 (m, 21H), 1.30–1.62 (m, 4H), 1.72–2.0 (m, 3H), 2.10–2.19 (m, 1H), 2.66 (dt, J=11.5, 4.0 Hz, 1H), 3.90 (d, J=16.6 Hz, 1H), 4.07 (d, J=16.6Hz, 1H), 5.07 (dt, J=10.6, 4.0 Hz, 1H), 7.16–7.30 (m, 5H). Anal. Calcd for C$_{23}$H$_{38}$O$_3$Si: C, 70.72; H, 9.81. Found: C, 70.79; H, 9.85.

1c(+): Colorless oil; $[\alpha]_D^{20}$+17.07° (c 3.29, CHCl$_3$); 1H NMR spectrum is identical to that of 1c(−).

The starting materials used in the preparation of 1 described above, i.e., (−)-menthol, benzyloxyacetyl chloride, (−)-(1R,2S)-2-phenyl-1-cyclohexanol, (+)-(1S,2R)-2-phenyl-1-cyclohexanol, tert-butyldimethylsilyl chloride, triisopropylsilyl chloride, are commercially available.

Imines used in reactions had the general formula 5 wherein:

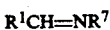

imine
2a: R$^1$=phenyl
2b: R$^1$=4-methoxyphenyl
2c: R$^1$=3,4-dimethoxyphenyl
2a,b,c: R$^7$=trimethylsilyl N-trimethylsilylaldimines used in these syntheses can readily be obtained by the reaction of lithium hexamethylsilazide with aldehydes. Typical procedure is described for the preparation of N-trimethylsilylbenzaldimine (2a): In 75 mL of anhydrous THF were added 17.29 mL (75 mmol) of hexamethyldisilazane and 30 mL (75 mmol) of n-butyllithium (2.5M in hexane) at 0° C. under nitrogen. After stirring for 1 h, 7.65 mL (75 mmol) of benzaldehyde was added at room temperature, and the mixture was refluxed for 3 h. Then, 9.52 mL (75 mmol) of freshly distilled trimethylsilyl chloride was added via a syringe. The mixture was refluxed for 2 h. White precipitate came out during this process. The reaction mixture was then cooled to room temperature and the liquid layer was transferred to a distillation flask under nitrogen via a syringe. The solvent was evaporated in vacuo, and the oily residue was distillated under reduced pressure (68° C./1 mm Hg) to give pure 2a as a pale yellow oil (10.6 g, 80%): 1H NMR (CDCl$_3$) δ 0.18 (s, 9 H), 7.33–7.36 (m, 3H), 7.72–7.75 (m, 2H), 8.89 (s, 1H); 13C NMR (CDCl$_3$) δ −1.25, 128.34, 128.39, 131.96, 138.70, 168.32.

In the same manner, 2b and 2c were prepared from 4-methoxybenzaldehyde and 3,4-dimethoxybenzaldehyde, respectively, in 78–82% yields.

2b: Pale yellow oil; bp 105° C./0.4 mmHg; 1H NMR (CDCl$_3$) δ 0.00 (s, 9H), 3.60 (s, 3H), 6.69 (d, J=8.7 Hz, 2H), 7.50 (d, J=8.7 Hz, 2H), 8.66 (s, 1H).

2c: Colorless oil; bp 140° C./0.2 mmHg; 1H NMR δ 0.00 (s, 9H), 3.67 (s, 3H), 3.71 (s, 3H), 6.65 (d, J=8.2 Hz, 1H), 7.01 (dd, J=8.2, 1.8 Hz, 1H), 7.22 (d, J=1.8 Hz, 1H), 8.63 (s, 1H).

The materials used in the preparation of imines 2, benzaldehyde, 4-methoxybenzaldehyde, 3,4-dimethoxybenzaldehyde, hexamethyldisilazane, trimethylsilyl chloride, and n-butyllithium, are readily commercially available.

A. Chiral enolate-imine cyclocondensation reactions were run for the asymmetric synthesis of 3-triisopropyl-silyloxy-4-arylazetidin-2-ones, 3-B(+), B(−), 3-C(+)

and 3-D(+). To a solution of diisopropylamine (223 mg, 2.20 mmol) in tetrahydrofuran (THF) (2.0 mL) was added 2.5M solution of n-butyllithium (2.20 mmol) in THF (1.0 mL) at 0° C. The solution was stirred for 30 min at 0° C. and then cooled to −78° C. To the mixture was added a solution of 1c(−) or 1c(+) (781 mg, 2.2 mmol) in THF (2.0 mL). The solution was stirred for 2 h followed by addition of a solution of N-trimethylsilylaldimine (2a–c) (2.0 mmol) in THF (2.0 mL). The mixture was stirred at −78° C. for 4 h, and then slowly allowed to warm to room temperature, and further stirred overnight. The reaction was quenched with saturated aqueous solution of ammonium chloride (50 mL), and the reaction mixture was extracted with chloroform (25 mL×3). The combined extracts were dried over anhydrous magnesium sulfate and concentrated in vacuo. The residue was submitted to a short column chromotography on silica gel using hexane/EtOAc (6/1) as the eluant to give the corresponding β-lactam (3-B,C,D) in 80–85% isolated yield.

B. In the same manner, 3-(tert-butyldimethylsilyloxy)-4-phenylazetidin-2-one (3-A) was synthesized in 52% yield by the chiral enolate - imine cyclocondensation of (−)-menthyltert-butyldimethylsilyloxyacetate (1a) with N-trimethylsilylbenzaldimine (2a).

C. The absolute configurations of the β-lactam products were determined by chemical correlation with authentic samples as follows: 3-A and 3-B were converted to (R)-3-phenyllactic acid and (2R,3S)-3-phenylisoserine, respectively. For 3-C(+) and 3-D(+), absolute configurations were assessed by analogy with 3-B(+) based on specific rotations and retention times on high performance liquid chromatography (HPLC) analyses on a chiral column.

D. Enantiomeric purity was determined by $^1$H NMR analysis using a chiral shift reagent, (+)-Eu(hfc)$_3$ for example 1, and HPLC analysis on a chiral column, DIACEL CHIRACEL OD (J. T. Baker Co.), using n-hexane/2-propanol as the solvent for examples 2–6.

The results are summarized in Table 1:

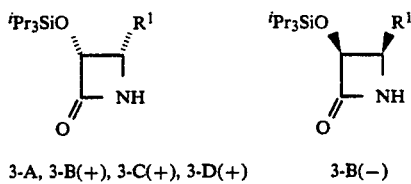

3-A, 3-B(+), 3-C(+), 3-D(+)    3-B(−)

Identification data for the β-lactams 3A–D are shown below:

3-A (obtained from the reaction in example 2): $[\alpha]_D^{20}$ −59.3 (c 1.00, CHCl$_3$); $^1$H NMR (CDCl$_3$) δ −0.18 (s, 3H), −0.04 (s, 3H), 0.635 (s, 9H), 4.80 (d, J=4.7 Hz, 1H), 5.05 (dd, J=4.7, 2.7 Hz, 1H), 6.30 (bs, 1H), 7.30–7.39 (m, 5H); $^{13}$C NMR (CDCl$_3$) δ −5.46, −4.95, 17.78, 25.23, 59.13, 79.57, 127.97, 128.04, 136.25, 169.73. High resolution mass spectrum (HRMS) Calcd for C$_{15}$H$_{23}$NO$_2$Si: 277.1497. Found: 277.1509.

3-B(+): mp 78°–79° C.; $[\alpha]_D^{20}$ +56.82° (c 1.10, CHCl$_3$); IR (KBr disk) 3264 ($\nu$NH), 1766 ($\nu$CO) cm$^{-1}$; $^1$H NMR (CDCl$_3$) δ 0.86–0.91 (m, 21H), 4.81 (d, J=4.7 Hz, 1H), 5.17 (dd, J=4.7, 2.6 Hz, 1H), 6.22 (bs, 1H), 7.30–7.40 (m, 5H). HRMS Calcd for C$_{18}$H$_{29}$NO$_2$Si: 319.1967. Found: 319.1969.

3-B(−): mp 77°–79° C.; $[\alpha]_D^{20}$ −55.83° (c 1.20, CHCl$_3$). The $^1$H NMR spectrum was identical to that of 3-B(+).

3-C(+): $[\alpha]_D^{20}$ 30 34.26 (c 1.08, CHCl$_3$); IR (KBr disk) 3276 ($\nu$NH), 1770 ($\nu$CO), 1514 ($\delta$NH) cm$^{-1}$; $^1$H NMR (CDCl$_3$) δ 0.80–0.89 (m, 21H), 3.73 (s, 3H), 4.68 (d, J=4.6 Hz, 1H), 5.05 (dd, J=4.6, 2.5 Hz, 1H), 6.35 (bs, 1H), 6.80 (d, J=8.7 Hz, 2H), 7.18 (d, J=8.7 Hz, 2H). HRMS Calcd for C$_{19}$H$_{31}$NO$_3$Si: 349.2073. Found: 349.2075.

3-D(+) mp 99°–101° C.; $[\alpha]_D^{20}$ +23.11° (c 1.32, CHCl$_3$); IR (KBr disk) 3309 ($\nu$NH), 1758sh, 1735 ($\nu$CO), 1517 ($\delta$NH) cm$^{-1}$; $^1$H NMR (CDCl$_3$) δ 0.89–0.98 (m, 21H), 3.87 (s, 3H), 3.88 (s, 3H), 4.76 (d, J=4.7 Hz, 1H), 5.14 (dd, J=4.7, 2.7 Hz, 1H), 6.22 (bs, 1H), 6.82–7.00 (m, 3H). HRMS Calcd for C$_{20}$H$_{33}$NO$_4$Si: 379.2179. Found: 379.2177.

TABLE 1

Asymmetric synthesis of β-lactams (3) through chiral enolate-imine cyclocondensation

| Example | Ester | Imine | β-Lactam | Isolated Yield (%) | Configuration | Enantiomeric Purity (% e.e.) |
|---|---|---|---|---|---|---|
| 1 | 1a | 2a | 3-A | 52 | 3R,4S | 50 |
| 2 | 1b | 2a | 3-A | 90 | 3R,4S | 76 |
| 3 | 1c(−) | 2a | 3-B(+) | 85 | 3R,4S | 96 |
| 4 | 1c(+) | 2a | 3-B(−) | 80 | 3S,4R | 97 |
| 5 | 1c(−) | 2b | 3-C(+) | 80 | 3R,4S | 96 |
| 6 | 1c(−) | 2a | 3-D(+) | 80 | 3R,4S | 98 |

1a: R$^4$ = t-BuMe$_2$Si; Xc = (−)-menthyloxy
1b: R$^4$ = t-BuMe$_2$Si; Xc = (−)-trans-2-phenyl-1-cyclohexyloxy
1c(−): R$^4$ = i-Pr$_3$Si; Xc = (−)-trans-2-phenyl-1-cyclohexyloxy
1c(+): R$^4$ = i-Pr$_3$Si; Xc = (+)-trans-2-phenyl-1-cyclohexyloxy
2a: R$^1$ = Ph; R$^7$ = Me$_3$Si
2b: R$^1$ = 4-MeOC$_6$H$_4$; R$^7$ = Me$_3$Si
2c: R$^1$ = 3,4-(MeO)$_2$C$_6$H$_3$; R$^7$ = Me$_3$Si The formulas for β-lactam products 3A–D after recovery of the chiral auxiliary Xc—H and deprotection (i.e., removal of R$^7$; R$^7$ was trimethylsilyl in these cases) during the workup were as follows:

As shown in Table I, the use of a chiral auxiliary and the oxygen protecting group exert effects on the enantioselectivity as well as on the chemical yield. Reactions of 1c bearing (−)- or (+)-trans-2-phenyl-1-cyclohexyl as the chiral auxiliary moiety (Xc) and triisopropylsilyl as the O-protecting group (R$^4$) in the hydroxyacetate precursor with imines 2a–c gave exclusively the corresponding cis-β-lactams in high yields with extremely high enantiomeric purity (96–98%ee) as shown in examples 3–6. When (−)-menthyl was used as the chiral auxiliary moiety (Xc) and tert-butyldimenthylsilyl (t-BuMe$_2$Si) was used as the O-protecting group (R$^4$), as in example 1, the reaction with the imine 1a gave 3-A in 52% yield and with 50% enantiomeric purity (%e.e.). The reaction of 1b bearing (−)-trans-2-phenyl-1-cyclohexyl as the chiral auxiliary moiety (Xc) and tert-butyl-dimethylsilyl as the O-protecting group (R$^4$), with 2a gave 3-A in 90% yield with 75% e.e. in example 2.

EXAMPLE 7

Preparation of
(3R,4s)-3-hydroxy-4-phenylazetidin-2-one (4)

A solution of β-lactam 3-B(+) (338 mg, 1.06 mmol) in 6 mL THF was treated with tetra-n-butylammonium fluoride (2.0 mL of 1M solution in THF) at room temperature for 40 min. under nitrogen. The reaction mixture was poured into water and extracted with ethyl acetate (20 mL×3). The combined organic extracts were dried over anhydrous magnesium sulfate and concentrated in vacuo. The residue was submitted to a short column chromatography on silica gel using ethyl acetate as the eluant to give 4 (168 mg, 97%) as a colorless solid.

Identification data for 4 are shown below:
4: mp 187°-188° C.; [α]$_D^{20}$+198.8° (c 1.0, MeOH); IR (KBr disk) 3370 ($\nu$OH), 3252 ($\nu$NH), 1743 ($\nu$CO) cm$^{-1}$; $^1$H NMR (CDCl$_3$) δ 2.32 (bs, 1H), 4.95 (d, J=5.0 Hz, 1H), 5.12 (m, 1H), 6.27 (bs, 1H), 7.30-7.47 (m, 5H); $^1$H NMR (DMSO-d$_6$) δ 4.70 (d, J=4.9 Hz, 1H), 4.94 (ddd, J=2.3, 4.9, 7.2 Hz, 1H), 5.82 (bs, 1H), 7.32-7.42 (m, 5H), 8.47 (bs, 1H).

EXAMPLE 8

Synthesis of (2R,3S)-3-phenylisoserine (5): A solution of β-lactam 4 (200 mg, 1.23 mmol) in 6N hydrochloric acid (8.0 mL) was stirred at 60° C. for 12 h. The reaction mixture was concentrated in vacuo to dryness, giving (2R,3S)-3-phenylisoserine hydrochloride (5.HCl) as a white solid (268 mg, 100%).

Alternatively, a mixture of β-lactam 3-B(+) (640 mg, 2.00 mmol) and 6N hydrochloric acid (8.0 mL) was stirred at 60° C. for 12 h, concentrated in vacuo to dryness to give 5.HCl as a white solid (437 mg, 100%).

Identification data for 5a.HCl are shown below:
5a.HCl: MP 222°-224° C. (dec.); [α]$_D^{20}$−14.6° (c 1.03, 6N HCl) [literature value (Ref) [α]$_D^{20}$−14.6° (6N HCl)]; IR (KBr disk) 3456 ($\nu$OH), 3300-2200 ($\nu$OH, $\nu$NH), 1732 ($\nu$CO), 1589 ($\delta$NH) cm$^{-1}$; $^1$H NMR (DMSO-d$_6$) δ 4.30-4.50 (m, 2H), 6.65 (bs, 1H), 7.38-7.45 (m, 3H), 7.50-7.55 (m, 2H), 8.65 (bs, 3H), 12.99 (bs, 1H).

Ref: Honig, H.; Senfer-Wasserthal, P.; Weber, H. Tetrahedron, 1990, 46, 3841.

Other β-lactams synthesized by the method of the invention can be converted to enantiomerically pure isoserines in the same manner.

EXAMPLE 9

Synthesis of N-benzoyl-(2R,3S)-3-phenylisoserine (6a): To a solution of compound 5.HCl (219 mg, 1.00 mmol) in water (10 mL) containing sodium bicarbonate (500 mg, 5.95 mmol) was added a solution of benzoyl chloride (0.14 mL, 1.20 mmol) in dichloromethane (5.0 mL). The mixture was vigorously stirred for 16 h at room temperature. The reaction mixture was acidified with 0.1N HCl and the crude product was extracted with ethyl acetate (40 mL×3). The combined organic extracts were dried over anhydrous magnesium sulfate and concentrated in vacuo to dryness. The residue was purified on a short silica gel column using chloroform/methanol (2/1) as the eluant to give N-benzoyl-(2R,3S)-3-phenylisoserine (6) (205 mg, 72%) as a white solid.

Identification data for 6 are shown below:
6a: mp 167°-169° C. [literature value (Ref) 168°-169°]; [α]$_D^{25}$−37.8.° (c 0.9, EtOH) [literature value (Ref) [α]$_D^{25}$+36.5° (c 1.45, EtOH) for (2S,3R)-isomer]; IR (KBr disk) 3600-2200 ($\nu$OH, $\nu$NH), 1710 ($\nu$CO), 1624 ($\nu$CO), 1523 ($\delta$NH) cm$^{-1}$; $^1$H NMR (D$_2$O) δ 4.43 (bs, 1H), 5.45 (bs, 1H), 7.30-7.43 (m, 5H), 7.50-7.75 (m, 5H). 1H-NMR (DMSO-d$_6$): δ 3.38 (bs, 1H), 3.84 (bs, 1H), 5.14 (bs, 1H), 7.10-7.40 (m, 5H), 7.52 (m, 3H), 7.82 (m, 2H), 9.76 (bs, 1H).

Ref: Harada, K.; Nakajima, Y. Bull. Chem. Soc. Jpn., 1974, 47, 2911.

EXAMPLES 10-17

A. The chiral enolate-imine cyclocondensations were carried out by reacting (−)-trans-2-phenyl-1-cyclohexyl triisopropyloxyacetate (1c(−)) with lithium diisopropylamide to generate the corresponding chiral enolate, followed by the addition of N-(4-methoxyphenyl)aldimines (7) in THF at −78° C. to give the corresponding β-lactams (8) according to Scheme 4. Experimental procedure for these reactions is virtually the same as that described in Examples 1-6. The results are summarized in Table 2.

N-(4-Methoxyphenyl)aldimines (7a-h) are readily prepared by condensation of aldehydes with p-anisidine. A typical procedure is described for the preparation of N-(4-methoxyphenyl)-(4-fluoro)benzaldimine (7b): To a solution of 4.81 g (39 mmol) of p-anisidine in 60 mL of dichloromethane was added 4.85 g (39 mmol) of p-fluorobenzaldehyde. The mixture was stirred over anhydrous magnesium sulfate at room temperature for 15 h. The dehydration agent was filtered off and the filtrate was concentrated in vacuo to give the crude imine. The crude imine was recrystallized from hexane/dichloromethane to give 7.69 g (86%) of pure 7b as white needles: Mp 99° C.; $^1$ NMR (CDCl$_3$) δ 3.81 (s, 3 H), 3.84 (s, 3 H), 6.91 (d, J=8.6, 2 H), 6.96 (d, J=8.8, 2 H), 7.20 (d, J=8.8, 2 H), 7.82 (d, J=8.6, 2 H), 8.39 (s ,1 H).

In the same manner, other N-(4-methoxylphenyl)aldimines were prepared in high yields. Identification data for 7a and 7c-h are shown below.

N-(4-Methoxyphenyl)benzaldimine (7a): White solid: mp 71°-72° C.; $^1$H NMR (CDCl$_3$) δ 3.93 (s, 3H), 6.93 (d,J=8.8 Hz, 2H, 7.23 (d, J=8.8 Hz, 2H); 7.46(m, 3H), 7.87 (m, 2H), 8.48 (s, 1H).

N-(4-Methoxyphenyl)-(4-trifluoromethyl)benzaldimine (7c): White needles; mp 124° C.; $^1$ NMR (CDCl$_3$) δ 3.81 (s, 3 H), 3.84 (s, 3 H), 6.91 (d, J=8.6 Hz, 2 H), 6.96 (d, J=8.8 Hz, 2 H), 7.20 (d, J=8.8 Hz, 2 H), 7.82 (d, J=8.6 Hz, 2 H), 8.39 (s, 1 H).

N-(4-Methoxyphenyl)furfuraldimine (7d): $^1$H NMR (CDCl$_3$) δ 3.82 (s, 3 H), 6.54 (dd, J=3.5, 1.8 Hz, 1 H), 6.90 (d, J=3.5 Hz, 1 H), 6.92 (d, J=8.9 Hz, 2 H), 7.26 (d, J=8.9 Hz, 2 H), 7.59 (d, J=1.8 Hz, 1 H), 8.31 (s, 1 H).

N-(4-Methoxyphenyl)-3-phenylpropenaldimine (7e): Yellow leaves: mp 119°-121° C.; $^1$H NMR (CDCl$_3$) δ 3.81 (s, 3H); 6.90-7.60 (m,7H), 8.28 (m, 1H) (ca. 1:1 mixture of stereoisomers).

N-(4-Methoxyphenyl)-3-furanylpropenaldimine (7f): Yellow needles: mp 71°-73° C.; $^1$H NMR (CDCl$_3$) δ 3.78 (s, 3H), 6.45 (dd, J=3.4, 1.6 Hz, 1H), 6.52 (d, J=3.4 Hz, 1H), 6.87 (d, J=15.8 Hz, 1H), 6.90 (d, J=8.9 Hz, 2H) 6.98 (dd, J=15.8, 8.7 Hz, 1H), 7.18 (d, J=8.9 Hz, 2H), 7.46 (d, J=1.6 Hz, 1H), 8.20 (d, J=8.7Hz, 1H).

N-(4-Methoxyphenyl)-3-methylbutanaldimine (7g): Yellow oil; $^1$H NMR (CDCl$_3$) δ 1.02 (d, J=6.7 Hz, 6H), 2.03 (m, 1H), 2.33 (dd, J=6.9, 5.3 Hz, 2H), 3.78 (3, 3H), 6.86 (d, J=8.8 Hz, 2H), 7.03 (d, J=8.8 Hz, 2H), 7.86 (t, J=5.3 Hz, 1H).

N-(4-Methoxyphenyl)cyclohexylacetaldimine (7h): Yellow oil; $^1$H NMR (CDCl$_3$) δ 1.00-1.80 (m, 11 H), 2.34 (dd, J=6.7, 5.4 Hz, 2 H), 3.79 (s, 3 H), 6.86 (d, J=8.9 Hz, 2 H), 7.02 (d, J=8.9 Hz, 2 H), 7.86 (t, J=5.4 Hz, 1 H); IR (neat) 3033-2849, 1505, 1244, 1038, 803 cm$^{-1}$.

The starting materials used in the preparation of 7, p-anisidine, benzaldehyde, 4-fluorobenzaldehyde, 4-trifluoromethylbenzaldehyde, cinnamaldehyde, 3-furanylpropenal, isobutylaldehyde, and cyclohexylacetaldehyde, are readily available.

B. The absolute configurations of the β-lactam products were determined by chemical correlation with authentic samples as follows: 8a was converted to 3-B(+); 8g and 8h were converted to norstatine and (2R,3S)-3-amino-2-hydroxy-4-cyclohexylbutanoic acid hydrochloride. For 8b-f, absolute configurations were assessed by analogy with 8a, 8g, and 8h based on retention times on the chiral HPLC analyses described above.

C. Enantiomeric purity was determined by HPLC analysis on a chiral column, DIACEL CHIRACEL OD (J. T. Baker Co.), using n-hexane/2-propanol as the solvent.

Identification data for 8a-h are shown below:

8a: $^1$H NMR (CDCl$_3$) δ 0.88-1.02 (m, 21 H), 3.73 (s, 3 H), 5.14 (d, J=5.0 Hz, 1 H), 5.23 (d, J=5.0 Hz, 1 H), 6.77 (d, J=9.0 Hz, 2 H), 7.28 (d, J=9.0 Hz, 2 H), 7.33 (m, 5 H); $^{13}$C NMR (CDCl$_3$) δ 11.72, 17.42, 17.48, 55.36, 63.27, 77.79, 114.25, 118.65, 128.16, 128.24, 128.30, 130.96, 134.04, 156.10, 165.66.

8b: White solid; mp 121°-122° C.; [α]$_D^{20}$+82.5° C. (c 0.724, CHCl$_3$); $^1$H NMR (CDCl$_3$) δ 0.82-0.84 (m, 18 H), 0.86-1.01 (m, 3 H), 3.62 (s, 3 H), 5.02 (d. J=4.9 Hz, 1 H), 5.11 (d, J=4.9 Hz, 1 H), 6.68 (d, J=6.9 Hz, 2 H), 6.96-7.25 (m, 6 H); IR (CHCl$_3$) (3050), 2974, 2868, 1748 cm$^{-1}$.

8c: White solid; mp 132°-133° C.; [α]$_D^{20}$+89.7° C. (c 0.925, CHCl$_3$); $^1$H NMR (CDCl$_3$) δ 0.87-1.15 (m, 21 H), 3.74 (s, 3 H), 5.21 (d, J=4.9 Hz, 1 H), 5.27 (d, J=4.9 Hz, 1 H), 6.79 (d, J=8.0 Hz, 2 H), 7.25 (d, J=8.0 Hz, 2 H), 7.46 (d, J=8.0 Hz, 2H), 7.60 (d, J=8.0 Hz, 2 H); IR (CHCl$_3$) (3050), 2975, 2868, 1750, 878 cm$^{-1}$.

8d: White solid; mp 109°-110° C.; $^1$H NMR (CDCl$_3$) δ 0.98-1.10 (m, 21 H), 3.75 (s, 3 H), 5.20 (d, J=4.9 Hz, 1 H), 5.24 (d, J=4.9 Hz, 1 H), 6.35-6.40 (m, 2 H), 6.81 (d, J=9.0 Hz, 2 H), 7.30 (d, J=9.0 Hz, 2 H), 7.42 (m, 1 H); $^{13}$C NMR (CDCl$_3$) δ 11.96, 17.52, 17.57, 55.43, 57.19, 78.13, 110.23, 110.63, 114.44, 118.55, 131.08, 142.80, 148.51, 156.45, 165.27.

8e: White solid; mp 127°-129° C., [α]$_D^{25}$−76.2 (c 1.04, CHCl$_3$); IR (KBr) 2944, 2865, 1879, 1743, 1654, 1647, 1513, 1460, 1389, 1366 cm$^{-1}$; $^1$H NMR (CDCl$_3$) δ 1.02-1.18 (m, 21H), 3.75 (s, 3H), 4.74 (dd, J=4.9, 8.9 Hz, 1H), 5.16 (d, J=4.9 Hz, 1H), 6.35 (dd, J=16.0, 8.9 Hz, 1H), 6.76-6.84 (m, 3H), 7.26-7.48 (m, 7H).

8f: White solid; mp 103.5°-105.5° C.; IR (KBr) 2948, 2866, 1743, 1513, 1389, 1246, 1181, 1120 cm$^{-1}$; $^1$H NMR (CDCl$_3$) δ 1.05-1.09 (m, 21H), 3.76 (s, 3H), 4.69 (dd, J=4.9, 8.6 Hz, 1H), 5.15 (d, J=4.9 Hz, 1H), 6.25 (dd, J=8.6, 16.0 Hz, 1H), 6.29 (d, J=3.3 Hz, 1H), 6.37 (dd, J=1.8, 3.3 Hz, 1H), 6.57 (d, J=16.0 Hz, 1H), 6.83 (m, 2H), 7.34-7.41 (m, 3H); $^{13}$C NMR (CDCl$_3$) δ 12.11, 17.70, 17.74, 55.54, 61.94, 77.18, 78.45, 107.88, 108.42, 111.26, 114.54, 118.70, 123.46, 123.82, 142.46, 190.99.

8g: Pale yellow solid; mp 59°-60° C.; $^1$H NMR (CDCl$_3$) δ 0.96 (d, J=6.4 Hz, 3 H), 1.03 (d, J=6.4 Hz, 3 H), 1.10-1.30 (m, 21 H), 1.60-1.68 (m, 1 H), 1.70-1.92 (m, 2 H), 3.75 (s, 3 H), 4.16-4.22 (m, 1 H), 5.06 (d, J=5.1 Hz, 1 H), 6.86 (d, J=9.0 Hz, 2 H), 7.32 (d, J=9.0 Hz, 2 H); $^{13}$C NMR (CDCl$_3$) δ 12.34, 17.82, 17.91, 22.18, 23.37, 25.34, 35.89, 55.50, 57.33, 76.34, 114.52, 118.73, 131.00, 156.29, 165.58; IR (KBr) 2946, 1742, 1513, 1458, 1249 cm$^{-1}$.

8h: Low melting point solid; $^1$H NMR (CDCl$_3$) δ 0.85-1.95 (m, 34 H), 3.78 (s, 3 H), 4.19-4.25 (m, 1 H), 5.05 (d, J=5.1 Hz, 1 H), 6.86 (d, J=9.0 Hz, 2 H), 7.32 (d, J=9.0 Hz, 2 H); $^{13}$C NMR (CDCl$_3$) δ 12.15, 17.76, 17.83, 26.12, 26.22, 26.47, 32.84, 34.22, 34.51, 55.36, 56.41, 76.13, 114.30, 118.45, 130.81, 155.99, 165.55; IR (film) 2925-2865, 1749, 1513, 1464, 1448, 1389, 1246, 1174, 1145, 1128, 939, 882, 828, 684 cm$^{-1}$.

TABLE 2

Asymmetric synthesis of β-lactams (8)

| Example | R8 | β-Lactam | Isolated Yield % | % ee. |
|---|---|---|---|---|
| 10 |  | 8a | 89 | 98 |
| 11 | 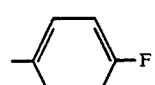 | 8b | 81 | 98 |
| 12 | 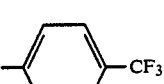 | 8c | 84 | 99 |
| 13 | 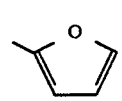 | 8d | 74 | 92 |
| 14 | 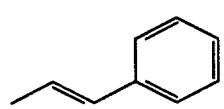 | 8e | 85 | 96 |
| 15 | 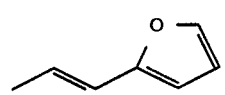 | 8f | 72 | 94 |
| 16 |  | 8g | 58 | 92 |

TABLE 2-continued

| | Asymmetric synthesis of β-lactams (8) | | | |
|---|---|---|---|---|
| Example | R8 | β-Lactam | Isolated Yield % | % ee. |
| 17 | 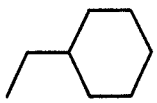 | 8h | 62 | 90 |

R⁴ = Triisopropylsilyl
Xc = (−)-trans-2-phenyl-1-cyclohexyl
R⁷ = N-4-methoxyphenyl

EXAMPLE 18

Synthesis of (2R,3S)-1-(4-methoxyphenyl)-3-triisopropylsilyloxy-4-(2-phenylethyl)azetidin-2-one (8i): A mixture of β-lactam 7e (436 mg, 0.97 mmol) in ethanol/ethyl acetate (2/1) and 10% Pd-C (100 mg) was stirred in a standard hydrogenation apparatus at 25° C. and atmospheric pressure of hydrogen for 10 h. Removal of the catalyst by filtration, followed by evaporation of the solvent afforded 420 mg (96% yield) of 8i as a white solid: $^1$H (CDCl$_3$) δ 1.03–1.20 (m, 21H), 2.15–2.35 (m, 2H), 2.70–2.82 (m, 2H), 3.75 (s, 3H), 4.14–4.20 (m, 1H), 5.09 (d, J=5.1 Hz, 1H), 6.82–6.86 (m, 2H), 7.16–7.31 (m, 7H); $^{13}$C NMR (CDCl$_3$) δ 11.99, 17.71, 17.79, 28.61, 31.55, 55.22, 57.73, 75.95, 114.24, 118.27, 125.87, 128.09, 128.30, 130.80, 141.25, 155.99, 165.33.

EXAMPLES 19-22

In the same manner as described in Example 7, β-lactams 8 obtained in Examples 10–17 Were converted to the corresponding 3-hydroxy-β-lactams (9) in nearly quantitative yields. Selected examples are shown below:

(3R,4s)-1-(4-Methoxyphenyl)-3-hydroxy-4-phenylazetidin-2-one (9a): Yellow solid; mp 211°–212° C.; $^1$H NMR (CDCl$_3$) δ 1.60–1.70 (bs, 1 H), 3.76 (s, 3 H), 5.18 (d, J=5.2 Hz, 1 H), 5.27 (d, J=5.2 Hz, 1 H), 6.81 (d, J=9.0 Hz, 2 H), 7.28–7.43 (m, 7 H); $^{13}$C NMR (CDCl$_3$) δ 55.46, 62.28, 77.33, 114.48, 118.85, 127.44, 128.97, 129.18, 133.22, 156.52, 165.25; IR (KBr disk) 3308, 3021, 2959, 2926, 2850, 1715, 1514, 1300, 1252, 1117, 837, 810 cm$^{-1}$.

(3R,4S)-1-(4-Methoxyphenyl)-3-hydroxy-4-(furan-2-yl) azetidin-2-one (9d): Yellow solid; mp 149°–152° C.; $^1$H NMR (CDCl$_3$) δ 2.97 (d, J=10.2 Hz, 1 H), 3.76 (s, 3 H), 5.20 (dd, J=10.2, 5.0 Hz, 1 H), 5.27 (d, J=5.0 Hz, 1 H), 6.43 (dd, J=3.3, 1.8 Hz, 1 H), 6.53 (bd, J=3.3 Hz, 1 H), 6.82 (d, J=9.0 Hz, 2 H), 7.30 (d, J=9.0 Hz, 2 H), 7.48 (dd, J=3.3, 0.6 Hz, 1 H); $^{13}$C NMR (CDCl$_3$) δ 55.50, 56.66, 77.94, 110.91, 111.02, 114.57, 118.79, 130.67, 143.85, 148.07, 156.81, 165.31; IR (KBr disk) 3369, 1743, 1509, 1397, 1298, 1240, 1119, 1028, 837, 808, 737, 726 cm$^{-1}$.

(3R,4S)-1-(4-Methoxyphenyl)-3-hydroxy-4-(2-methylpropyl)azetidin-2-one (9g): Yellow solid; mp 160°–163° C.; $^1$H NMR (CDCl$_3$) δ 0.99 (d, J=6.3 Hz, 3 H), 1.02 (d, J=6.3 Hz, 3 H), 1.70–1.90 (m, 3 H), 3.78 (s, 3 H), 4.19–4.25 (m, 1 H), 4.45–4.65 (bs, 1 H), 5.04 (d, J=5.0 Hz, 1 H), 6.86 (d, J=9.0 Hz, 2 H), 7.30 (d, J=9.0 Hz, 2 H); $^{13}$C NMR (CDCl$_3$) δ 22.35, 23.09, 25.55, 35.25, 55.54, 57.73, 75.49, 114.64, 119.21, 130.46, 156.71, 166.64; IR (KBr disk) 3312, 1723, 1709, 1514, 1243, 1180, 1036, 837, 805 cm$^{-1}$.

(3R,4S)-1-(4-Methoxyphenyl)-3-hydroxy-4-(cyclohexylmethyl)-azetidin-2-one (9h): Yellow solid; mp 152°–155° C.; $^1$H NMR (CDCl$_3$) δ 1.00–1.90 (m, 13 H), 3.79 (s, 3 H), 4.22–4.28 (m, 1 H), 5.02 (d, J=5.0 Hz, 1 H), 6.86 (d, J=9.0 Hz, 2 H), 7.30 (d, J=9.0 Hz, 2 H); $^{13}$C NMR (CDCl$_3$) δ 26.11, 26.19, 26.45, 33.19, 33.59, 33.70, 34.95, 55.47, 57.42, 75.36, 114.54, 119.13, 130.38, 156.59, 166.99; IR (KBr disk) 3309, 2922, 2849, 1712, 1515, 1445, 1407, 1300, 1245, 1123, 1033, 834, 806 cm$^{-1}$.

EXAMPLE 23

Synthesis of (2R,3S)-3-triisopropylsilyloxy-4-(2-phenylethyl)azetidin-2-one (3i): To a solution of β-lactam 7i (92 mg, 0.20 mmol) in acetonitrile (2 mL) was added slowly a solution of cerium ammonium nitrate (334 mg, 0.61 mmol) in water (3 mL) at 0° C. The mixture was stirred at 0° C. for 1 h and diluted with 15 mL of water. The mixture was then extracted with ethyl acetate (15 mL×3). The organic extracts were washed with 5% sodium bicarbonate (10 mL) and the aqueous extracts are washed with ethyl acetate (15 mL). The combined organic extracts were washed with 10% soduim sulfite (until the aqueous layer remained colorless), 5% sodium bicarbonate (10 mL), and brine. The combined extracts were dried over anhydrous sodium sulfate and concentrated in vacuo. The residue was purified on a short silica gel column using hexane/ethyl acetate (5/1) as the eluant to give 60 mg (85% yield) of 3i as a colorless oil: $^1$H NMR (CDCl$_3$) δ 1.02–1.18 (m, 21H), 1.91–2.06 (m, 2H), 2.68–2.76 (m, 2H), 3.68–3.74 (m, 1H), 4.96 (dd, J=4.8, 2.4 Hz, 1H), 6.07 (bs, 1H), 7.17–7.37 (m, 5 H). $^{13}$C NMR (CDCl$_3$) δ 11.94, 17.72, 17.79, 31.62, 32.32, 55.60, 77.80, 126.04, 128.29, 128.49, 141.23, 169.91.

EXAMPLES 24-26

Transformation of N-(4-methoxyphenyl)-β-lactam 7 to β-lactam 3: In the same manner as described in Example 19, other β-lactams 7 obtained in Examples 10–17 were converted to the corresponding deprotected β-lactams 3. Selected Examples are shown below:

(3R,4S)-3-Triisopropylsilyloxy-4-(furan-2-yl)azetidin-2-one (3d): Yellow solid; mp 58°; $^1$H NMR (CDCl$_3$) δ 0.95–1.10 (m, 21 H), 4.84 (d, J=4.6 Hz, 1 H), 5.17 (dd, J=4.6, 2.2 Hz, 1 H), 6.14 (bs, 1 H), 6.37–6.39 (m, 2 H), 7.40–7.42 (m, 1 H).

(3R,4S)-3-Triisopropylsilyloxy-4-(2-methylpropyl)azetidin-2-one (3g): $^1$H NMR (CDCl$_3$) δ 0.93 (d,J=6.6Hz,3H), 0.96 (d,J=6.6.Hz,3H), 1.05–1.25 (m,22H),1.52 (m,1H), 1.67 (m,1H),3.78 (ddd,J=7.4,5.5, 5.4 Hz,1H), 4.96 (dd,J=4.8, 2.4 Hz, 1H), 6.02 (bs, 1H); $^{13}$C NMR (CDCl$_3$) δ 12.12, 17.72, 17.80, 22.29, 23.08, 25.35, 39.08, 54.45, 78.04, 170.00; IR (neat) 3238, 1759, 1465, 1184 cm$^{-1}$.

(3R,4S)-3-Triisopropylsilyloxy-4-(cyclohexylmethyl)azetidin-2-one (3h): Yellow oil; $^1$H NMR (CDCl$_3$) δ 0.97–1.25 (m,32 H), 1.40–1 70 (m,2H), 3.80 (dt, J=8.4, 4.8Hz,1H), 4.95 (dd,J=4.8, 2.4Hz, 1H), 6.05 (bs, 1H); $^{13}$C NMR (CDCl$_3$) δ 12.06, 17.77, 17.82, 26.16, 26.25, 26.46, 33.15, 33.82, 34.85, 37.72, 53.89, 77.98, 168.87; IR (neat) 3238, 1759, 1465, 1184 cm$^{-1}$.

EXAMPLE 27

Synthesis of (2R,3S)-3-triisopropylsilyloxy-4-(2-cyclohexylethyl)azetidin-2-one (3j): A mixture of β-lactam 3i (100 mg, 0.29 mmol) in methanol (10 mL) and 5% Rh-C catalyst (10 mg) was hydrogenated at 50° C. and 800 psi of hydrogen for 20 h. After the catalyst was filtered out and the solvents evaporated in vacuo, the residue was purified on a short siliga gel column using hexane/ethyl acetate (5/1) as the eluant to give 95 mg (93% yield) of 3j as a colorless liquid: $^1$H NMR (CDCl$_3$) δ 1.07-1.72 (m, 36H), 3.61-3.67 (m, 1H), 4.94 (dd, J=2.4, 4.8 Hz, 1H), 6.42 (bs, 1H); $^{13}$C NMR (CDCl$_3$) δ 12.02, 17.79, 26.31, 26.60, 27.54, 33.19, 33.39, 33.54, 37.71, 56.44, 77.74, 170.15.

EXAMPLES 28-31

Synthesis of (2R,3S)-3-substituted-isoserines (5): In the same manner as described for Example 8, β-lactam obtained from examples 18-22 were hydrolyzed with 6N hydrochloric acid to give the corresponding enantiomerically pure hydrochloric acid salts of (2R,3S)-3-substituted-isoserines in nearly quantitative yields.

Identification data for 5b-e are shown below:

(2R,3S)-3-Amino-2-hydroxy-5-phenylpentanoic acid hydrochloride (5b): White solid; $^1$H NMR (CD$_3$OD) δ 1.82-2.09 (m, 2H), 2.69 (t, J=8.1 Hz, 2H), 3.46 (m, 1H), 4.26 (d, J=3.1 Hz, 1H), 7.10-7.24 (m, 5H); $^{13}$C NMR (CD$_3$OD) d 30.92, 31.48, 52.78, 125.99, 127.89, 128.21, 140.12, 169.15.

(2R,3S)-3-Amino-2-hydroxy-5-cyclohexylpentanoic acid hydrochloride (5c): White solid; $^1$H NMR (CD$_3$OD) d 0.89-1.79 (m, 15H), 3.48 (m, 1H), 4.27 (d, J=3.6 Hz, 1H).

(2R,3S)-3-Amino-2-hydroxy-5-methylhexanoic acid hydrochloride (5d) White solid; $^1$H NMR (CD$_3$OD) δ 0.93 (d,J=6.9 Hz,3H), 0.95 (d, J=6.9 Hz, 3H), 1.33 (dt, J=13.7, 6.9 Hz, 1H), 1.47 (dt,J=13.7, 6.9 Hz, 1H), 1.75 (m, 1H), 3.19 (m,1H), 3.83 (d,J=2.3 Hz, 1H).

(2R,3S)-3-Amino-2-hydroxy-4-cyclohexylbutanoic acid hydrochloride (5e): White solid: $^1$H NMR (D$_2$O) δ 0.85-1.74 (m, 13H), 3.58 (m, 1H), 4.07 (d,J=3.6 Hz, 1H).

What is claimed is:

1. A process for the production of a hydroxyamino acid with high enantiomeric purity from a chiral β-lactam of the formula:

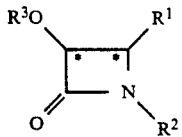

wherein
R$^1$ is as defined below in an imine;
R$^2$ is selected from the group consisting of hydrogen, and the groups for R$^7$ defined below in the imine;
R$^3$ is hydrogen or an oxygen protecting group R$^4$;
comprising reacting an O-protected hydroxyacetic acid derivative of the formula R$^4$OCH$_2$C(O)Xc wherein
R$^4$ is an oxygen protecting group;
Xc is a chiral auxiliary;
with a base of the formula

MNR$^5$R$^6$ wherein
M is an alkali metal;
R$^5$ and R$^6$ are independently selected from the group consisting of C$_1$-C$_{10}$ branched or straight chain alkyl, C$_3$-C$_{10}$ cycloalkyl and trialkylsilyl of C$_3$-C$_{18}$;

followed by cyclocondensing with an imine having the formula

R$^1$CH=NR$^7$ wherein
R$^1$ is selected from a group consisting of C$_1$-C$_{20}$ branched or straight chain alkyl, C$_3$-C$_{10}$ cycloalkyl, C$_2$-C$_{20}$ alkenyl, C$_2$-C$_{20}$ alkynyl, C$_6$-C$_{20}$ substituted aryl, C$_3$-C$_{20}$ heteroaromatic and C$_3$-C$_{20}$ substituted heteroaromatic; R$^7$ is selected from the group consisting of C$_1$-C$_{20}$ branched or straight chain alkyl, C$_3$-C$_{20}$ cycloalkyl, C$_2$-C$_{20}$ alkenyl, C$_2$-C$_{20}$ alkynyl, C$_6$-C$_{20}$ aryl, C$_6$-C$_{20}$ substituted aryl, C$_3$-C$_{20}$ heteroaromatic, C$_3$-C$_{20}$ substituted heteroaromatic and trisubstituted silyl of C$_3$-C$_{20}$ and hydrolyzing the β-lactam to produce the corresponding hydroxyamino acid.

2. The process of claim 2 wherein the oxygen protecting group R$^4$ has the formula 2:

R$^8$R$^9$R$^{10}$Y—   2 wherein
R$^8$, R$^9$ AND R$^{10}$ are independently selected from the group consisting of C$_1$-C$_{10}$ branched or straight chain alkyl, C$_1$-C$_{10}$ alkoxy, C$_3$-C$_{20}$ cycloalkyl, C$_2$-C$_{20}$ alkenyl, C$_2$-C$_{10}$ alkynyl, C$_6$-C$_{15}$ aryl, C$_6$-C$_{15}$ substituted aryl, C$_3$-C$_{15}$ aryloxy, C$_3$-C$_{20}$ substituted heteroaromatic, trialkylsilyl of C$_3$-C$_{18}$ and trialkysiloxy of C$_3$-C$_{18}$ and trialkylsiloxy of C$_3$-C$_{18}$;
Y is selected from the group consisting of carbon, silicon, germanium, and tin; or formula 3:

R$^{11}$R$^{12}$Z—   3 wherein
R$^{11}$ and R$^{12}$ are independently selected from the group consisting of C$_1$-C$_{10}$ branched or straight chain alkoxy, C$_3$-C$_{10}$ cycloalkyloxy, C$_6$-C$_{15}$ aryloxy, C$_6$-C$_{15}$ substituted aryloxy, C$_3$-C$_{20}$ heteroaromatic, C$_3$-C$_{20}$ substituted heteroaromatic, trialkylsilyl of C$_3$-C$_{18}$ and trialkylsiloxy of C$_3$-C$_{18}$; and
Z is boron or aluminum.

3. The process of claim 2 wherein R$^8$, R$^9$, and R$^{10}$ are independently selected from the group consisting of methyl, ethyl, propyl, isopropyl, butyl, isobutyl, sec-butyl, tert-butyl, pentyl, isopentyl, neopentyl, hexyl, isohexyl, t-hexyl, cyclohexyl, phenyl, tolyl, xylyl, biphenyl, napththyl, trimethylsilyl, triethylsilyl, dimethylphenyl silyl, diphenylmethyl silyl, trimethoxysilyl, triethoxylsilyl, methyldimethoxylsilyl, dimethylmethoxylsilyl, methoxy, ethoxyl, propoxy isopropoxy, butoxy, isobutyoxy, sec-butoxy, tert-butoxy, pentoxy, isopentoxy, neopentoxy, hexyloxy, isohexyloxy, t-hexyloxy, cyclohexyloxy, phenoxy, tolyloxy, xylyloxy, biphneyloxy, naphthyloxy, trimethysilyloxy, triethylsilyloxy, dimethylphenylsilyloxy, diphenylmethylsilyloxy, trimethoxysilyloxy, triethoxylsilyloxy, methyldimethoxysilyloxy, dimethylethoxysilyloxy; and R$^{11}$ and R$^{12}$ are independently selected from the group consisting of methoxy, ethoxyl, isopropoxy, isobutoxy, neopentyloxy, cyclohexyloxy, phenoxy, 2,4,6-trimethylphenoxy, 2,4,6-triisopropylphenoxy, and 2,6-di-tert-butyl-4-methyphenoxy.

4. The process of claim 2 wherein Y is silicon.

5. The process of claim 1 wherein R⁴ is selected from the group consisting of triisopropylsilyl, t-butyldimethylsilyl, tertbutyldiphenylsily, triethylsily, ditertbutylmethylsilyl, ditertbutylphenylsilyl, dimethylthexylsilyl, triisobutylsilyl, dicyclohexylmethysilyl, cyclohexyldimethylsilyl, diisopropyloctysilyl, diisobutyloctysilyl, and triphenylmethyl (trityl).

6. The process of claim 1 wherein Xc is derived from the corresponding Xc—H, wherein Xc—H is a chiral alcohol of $C_4$–$C_{20}$ with or without other functional groups.

7. The process of claim 6 wherein chiral alcohol has a functional group selected from the group consisting of N-protected amino, O-protected hydroxyl, S-protected mercapto, ether, sulfide, and sulfone.

8. The process of claim 6 wherein Xc—H is selected from the group consisting of (−)-menthol, (+)-neomenthol, (−)-borneol, isopinocampheneol, (+)- and (−)-trans-2-phenyl-1-cyclohexanol, (−)-10-dicyclohexylsulfamoyl-D-isoborneol, (−)-8-phenylmenthol, (+)-cinchonine, (−)-cinchonidine, quinine, quinidine, and N-methylephedrine.

9. The process of claim 1 wherein Xc is a chiral oxazolidinone of the formula

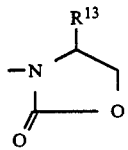

wherein
R¹³ is selected from $C_1$–$C_6$ branched or straight chain alkyl, $C_3$–$C_{15}$ cycloalkyl, $C_6$–$C_{15}$ aryl and $C_3$–$C_{20}$ substituted aryl, $C_3$–$C_{20}$ substituted heteroaromatic.

10. The process of claim 9 wherein R¹³ is isopropyl or phenyl.

11. The process of claim 1 wherein R¹ is selected from a group consisting of methyl, ethyl, propyl, isopropyl, butyl, isobutyl, sec-butyl, tert-butyl, pentyl, isopentyl, neopentyl, hexyl, isohexyl, t-hexyl, cyclopropyl, cyclobutyl, cyclopentyl, cycloheptyl, 2-(methylthio)ethyl, 4-(N,N-dibenzylamino)butyl, 4-[N,N-bis(trimethylsily)amino]-butyl, cyclohexylmethyl, cyclohexylethyl, 2-phenylethyl, 2-furanylethyl, 2-(N-acetylpyrrolyl)ethyl, 2-thienylethyl, 2-pyridinylethyl, phenyl, 4-methoxyphenyl, 4-acetoxylphenyl, 4-trifluoroacetoxylphenyl, 4-tert-butoxylcarbonyloxyphenyl, 4-benzyloxylcarbonyloxyphenyl, 4-trichloro-ethoxycarbonyloxyphenyl, 4-(9-fluororenylmethoxycarbonyloxy)phenyl, 4-tri-methylsilyloxyphenyl, 4-tert-butyldimethylsilyloxy-phenyl, 3,4-dimethoxyphenyl, 3,4-methylenedioxyphenyl, 3-methoxy-4-acetoxyphenyl, 3,4-diacetoxyphenyl, 3,4-bis(tert-butoxycarbonyloxy)phenyl, 3,4-bis(benzyloxycarbonyloxy)phenyl, 3,4-bis(trichloroethoxycarbonyloxy)phenyl, 3,4-bis(9-fluorenylmethoxy)phenyl, 3,4-bis(trimethylsilyloxy)phenyl, 3,4-bis-(tertbutyldimethylsilyloxy)phenyl, 4-(N,N-dimethylamino)-phenyl, 4-[N,N-dimethylamino)-phenyl, 4-[N,N-bis(trimethylsilyl)amino]phenyl, furanyl, thienyl, N-acetylpyrrolyl, pyridinyl, ethenyl, 2-phenylethenyl, 2-furanylethenyl, 2-indenylethenyl, trimethylsilylethynyl, phenylethynyl, furanylethynyl, thienylethynyl, (N-acetylpyrrolyl)ethynyl, and pyridinylethynyl.

12. The process of claim 11 wherein R¹ is selected from the group consisting of isobutyl, cyclohexylmethyl, phenyl, 2-phenylethenyl, and 2-furanylethenyl.

13. The process of claim 12 wherein R² is selected from the group consisting of hydrogen, methyl, ethyl, propyl, isopropyl, butyl, sec-butyl, tert-butyl, cyclohexyl, benzyl, diphenylmethyl, allyl, propargyl, trimethylsilylpropargyl, and 4-methoxyphenyl.

14. The process of claim 1 wherein R⁷ is selected from a group consisting of trimethylsilyl, p-methoxyphenyl, methyl, ethyl, propyl, isopropyl, butyl, sec-butyl, tertbutyl, cyclohexyl, benzyl, diphenylmethyl, allyl, propargyl, and trimethylsilylpropargyl.

15. The process of claim 1 wherein the hydroxyamino acid is selected from the group consisting of norstatine, (2R,3S)-3-amino-4-cyclohexyl-2-hydroxybutanoic acid (ACHBA) and (2R,3S)-3-phenylisoserine.

* * * * *

UNITED STATES PATENT AND TRADEMARK OFFICE
CERTIFICATE OF CORRECTION

PATENT NO. : 5,294,737
DATED : March 15, 1994
INVENTOR(S) : Ojima

It is certified that error appears in the above-identified patent and that said Letters Patent is hereby corrected as shown below:

Column 2, delete lines 49-61 and insert the following:

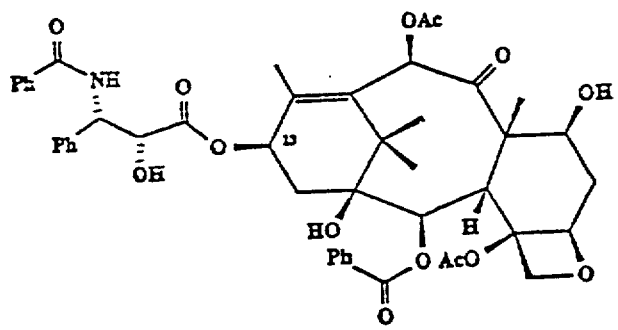

UNITED STATES PATENT AND TRADEMARK OFFICE
CERTIFICATE OF CORRECTION

PATENT NO. : 5,294,737

DATED : March 15, 1994

INVENTOR(S) : Ojima

It is certified that error appears in the above-identified patent and that said Letters Patent is hereby corrected as shown below:

Column 3, delete lines 1-14 and insert the following:

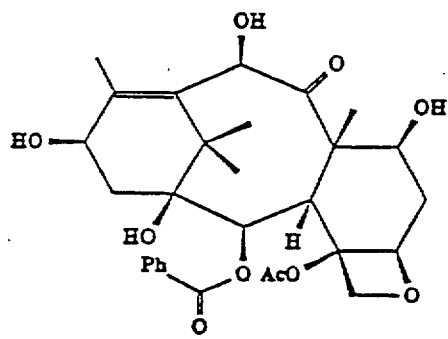

Column 16, line 13, after "59.3" insert --°--;
    line 29, delete "30" and insert --+--; after "34.26" insert --°--;

Column 24, line 25, delete "AND" and insert --and--;
    lines 52 and 53, delete "dimeth-ylphenyl silyl" and insert --dimethylphenylsilyl--; and delete "diphenylmethyl silyl" and insert --diphenylmethylsilyl--;

UNITED STATES PATENT AND TRADEMARK OFFICE
CERTIFICATE OF CORRECTION

PATENT NO. : 5,294,737             Page 3 of 4
DATED      : March 15, 1994
INVENTOR(S) : Ojima It is certified that error appears in the above-identified patent and that said Letters Patent is hereby corrected as shown below:

line 55, delete "ethoxyl" and insert --ethoxy--;

line 59, delete "trimethysilyloxy" and insert --trimethylsilyloxy--;

line 62, delete "dimethylethoxylsilyloxy" and insert --dimethylethoxysilyloxy--;

line 64, delete "ethoxyl" and insert --ethoxy--.

Column 25, line 3, delete "tertbutyldiphenylsily" and insert --terbutyldiphenylsilyl-- and delete "triethylsily" and insert --triethylsilyl--;

line 6, delete "diisopropyloctysilyl" and insert --diisopropyloctylsilyl-- and delete "diisobutyloctysilyl" and insert --diisobutyloctylsilyl--.

UNITED STATES PATENT AND TRADEMARK OFFICE
CERTIFICATE OF CORRECTION

PATENT NO. : 5,294,737
DATED : March 15, 1994
INVENTOR(S) : Ojima

It is certified that error appears in the above-identified patent and that said Letters Patent is hereby corrected as shown below:

Column 26, lines 10-11, delete "4-tri-methylsilyloxyphenyl" and insert --4-trimethylsilyloxyphenyl-- and delete "4-tert-butyldimethyl-silyloxy-phenyl" and insert --4-tert-butyldimethyl-silyloxyphenyl--;

line 17, delete "3,4-bis-(tertbutyldimethylsilyloxy)phenyl" and insert --3,4-bis-(tert-butyldimethylsilyloxy)phenyl--.

Signed and Sealed this

Fourth Day of April, 1995

Attest:

BRUCE LEHMAN

*Attesting Officer*    *Commissioner of Patents and Trademarks*